United States Patent
Ryu

(10) Patent No.: US 6,734,328 B1
(45) Date of Patent: May 11, 2004

(54) PROCESS FOR THE SELECTIVE HYDROGENATION OF ALKYNES

(75) Inventor: J. Yong Ryu, Pasadena, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 10/290,831

(22) Filed: Nov. 8, 2002

(51) Int. Cl.$^7$ .............................................. C07C 7/167
(52) U.S. Cl. ...................... 585/275; 585/265; 585/259; 585/260; 585/261; 585/262
(58) Field of Search ................................ 585/265, 259, 585/260, 261, 262

(56) References Cited

U.S. PATENT DOCUMENTS

| | | | |
|---|---|---|---|
| 4,440,956 A | 4/1984 | Couvillion | 585/260 |
| 4,493,906 A | 1/1985 | Couvillion | 502/346 |
| 4,533,779 A | 8/1985 | Boitiaux et al. | 585/259 |
| 4,831,200 A | 5/1989 | Debras et al. | 585/259 |
| 5,877,363 A | 3/1999 | Gildert et al. | 585/260 |
| 6,169,218 B1 | 1/2001 | Hearn et al. | 585/260 |
| 6,284,104 B1 | 9/2001 | Maraschino | 202/154 |
| 6,414,205 B1 | 7/2002 | Stanley et al. | 585/259 |

FOREIGN PATENT DOCUMENTS

| | | | |
|---|---|---|---|
| WO | WO 94/04477 A1 | 3/1994 | |
| WO | WO 95/15934 A1 | 6/1995 | |

*Primary Examiner*—Thuan D. Dang
(74) *Attorney, Agent, or Firm*—Kenneth H. Johnson

(57) ABSTRACT

An improved selective hydrogenation process for removing acetylenic impurities such as vinyl acetylene, ethyl acetylene, propyl acetylene and acetylene in a steam cracked crude butadiene stream by selective hydrogenation is carried out in two steps. In the first step, the partial selective hydrogenation is carried out in a fixed bed with a copper-based catalyst to have the ratio of vinyl acetylene to ethyl acetylene in a range of from 0 to about 1, preferably from about 0.01 to 0.6, in the product stream. In the second step, the selective hydrogenation of the remaining $C_4$ acetylenic impurities is carried out to completion in the catalytic distillation mode using a palladium promoted copper catalyst, an improved palladium catalyst or a combination of these two. The product stream from the first step partial hydrogenation is introduced to the catalytic distillation column at a position within the catalytic reaction zone and hydrogen feed gas is introduced below the catalyst bed to maximize the recovery of 1,3-butadiene. The feed position to the catalytic distillation column may vary along the catalyst loading zone depending on the feed composition from the first step selective hydrogenation reactor. Optionally, to prolong the catalyst service and cycle time, a solvent is added to the reactor with the hydrocarbon bed stream in the first step or the second step or both steps.

9 Claims, 1 Drawing Sheet

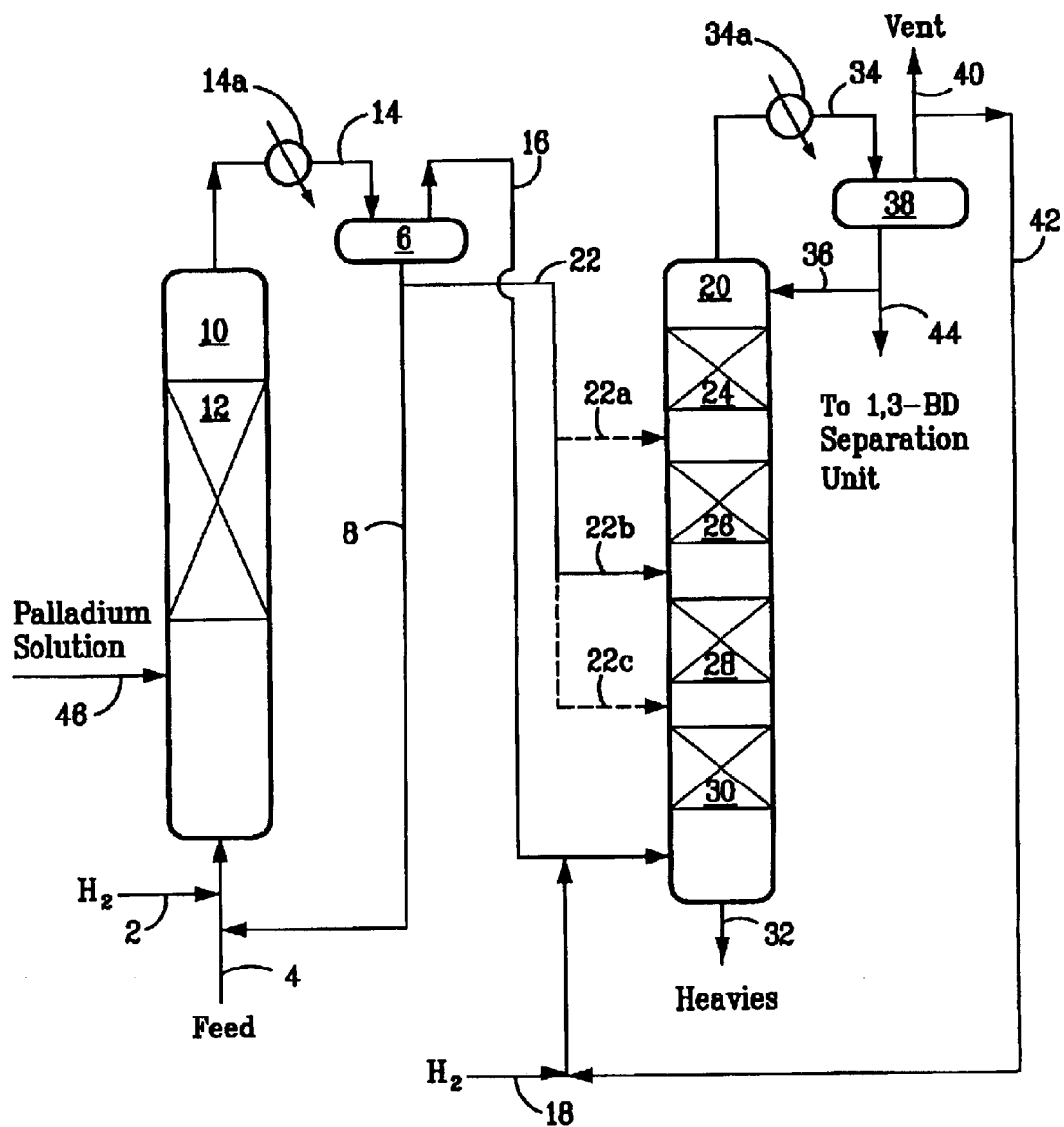

PROCESS FOR THE SELECTIVE HYDROGENATION OF ALKYNES

BACKGROUND OF THE INVENTION

1. Field of the Invention

The present invention relates to the selective removal of more highly unsaturated compounds from mixtures of unsaturated compounds. More particularly the invention is concerned with the selective hydrogenation of acetylenic compounds from mixtures with dienes, such as 1,3-butadiene. The invention provides a novel process for the selective hydrogenation of acetylenes in admixture with other unsaturated compounds.

2. Related Information

Crude butadiene streams contain undesired multi-unsaturated impurities such as vinyl acetylene, ethyl acetylene, methyl acetylene, etc. These impurities need to be removed to produce high quality 1,3-butadiene product. Although the acetylenes are more reactive in the hydrogenation, 1,3-butadiene is not inert under the selective hydrogenation condition, especially as the conversion of acetylenes approaches to near completion. The concentration of vinyl acetylene in the steam cracked crude butadiene stream is generally much higher than the concentration of ethyl acetylene. The reactivity of vinyl acetylene toward selective hydrogenation is higher than ethyl acetylene.

Complete or near complete recovery of 1,3-butadiene and complete removal of both vinyl acetylene and ethyl acetylene is highly desired. However, it is not possible to accomplish this objective in the current commercial processes. In current commercial practice, the selective hydrogenation is carried out in either fixed bed process or catalytic distillation process. Each has its own advantages. The fixed bed unit is easier and cheaper to operate, construct, replace spent catalyst with new catalyst, and regenerate spent catalyst. A catalytic distillation unit generally has higher recovery of 1,3-butadiene and longer catalyst cycle time. But it has higher cost for the catalyst loading and the deactivated catalyst needs to be removed from the distillation column instead of in-situ regeneration. Also catalytic distillation operation has one less independent process variable than fixed bed operation because the temperature is a function of pressure and composition of the materials in the catalytic distillation column.

Supported copper catalysts and palladium catalysts have been preferred catalysts in cleaning up acetylenic impurities in olefin streams by selective hydrogenation.

In general, the palladium catalysts are very active compared with the copper catalysts for selective hydrogenation of acetylenic compounds in the olefinic steams, but have lower selectivity for the acetylenes than copper-based catalysts. But the palladium catalysts exhibit low selectivity for retaining diolefins, such as 1,3-butadiene, when one is trying to remove high concentrations (>2000 ppm) of total alkynes to less than about 500 ppm total alkynes in the streams, especially when the acetylenes are reduced to less than 200 ppm. The non selectivity of palladium catalysts is not desirable in commercial practice, because it results in a loss of 1,3-butadiene. To improve olefin selectivity of palladium catalysts, silver or gold has been added to palladium catalysts in minor amounts as modifier.

On the other hand, the copper catalysts selectively hydrogenate acetylenic compounds without substantial hydrogenation of the olefins and diolefins (designated herein as selectivity for retaining olefins). But the activity of copper catalysts is low and the catalyst cycle time is undesirably short for the feed streams, containing higher than about 2000 ppm total alkynes due to fast deactivation caused by the deposition of polymeric material on the catalyst surface. Even though the hydrogenation may be carried out in liquid phase, some of the polymers deposited on the copper catalyst have little solubility in the liquid product stream under selective hydrogenation conditions. Due to these two reasons, the copper catalysts need improvement for the selective hydrogenation of the mixed olefin feeds, which contain relatively high concentration of total alkynes.

U.S. Pat. No. 4,533,779 disclosed palladium/gold catalysts supported on supports such as alumina (1 to 100 $m^2/g$) for selective hydrogenation of acetylenic compounds. The contents of palladium and gold in the catalysts were in the range of 0.03 to 1 weight % and 0.003 to 0.3 weight %, respectively.

U.S. Pat. No. 4,831,200 disclosed the process for the selective hydrogenation of alkynes in olefin streams such as mixtures with 1,3-butadiene. The selective hydrogenation was carried out in two steps in sequence. In the first step, the hydrocarbon feed was passed at least partially in liquid phase with hydrogen over the palladium catalyst such as that disclosed in U.S. Pat. No. 4,533,779 discussed above. In the second step, the product stream from the first step was passed again, at least partially in liquid phase, with hydrogen over a copper catalyst such as that disclosed in U.S. Pat. Nos. 4,493,906 and 4,440,956 discussed above to produce significantly reduced alkyne concentration in the final product stream.

It is an advantage of the present invention that it improves the two step process by combining a fixed bed selective hydrogenation and a catalytic distillation selective hydrogenation in a specific sequence to take advantage of the best characteristics of disparate systems for selective hydrogenation of $C_4$ acetylenes in a crude butadiene stream.

SUMMARY OF THE INVENTION

Briefly, the present invention is a process for removing $C_4$ acetylene impurities in a crude butadiene stream by selective hydrogenation in two steps. In the first step, the partial selective hydrogenation is carried out in a fixed bed reactor. In the second step, remaining $C_4$ acetylenes are completely removed.

In a preferred embodiment a hydrocarbon feed stream comprising acetylenic compounds and in vapor phase is introduced to the selective hydrogenation reactor, preferably a fixed bed reactor, in the presence of a liquid solvent to prolong the catalyst cycle time or service time. The solvent is recovered from the reactor effluent stream to recycle. Suitable solvents include $C_4$–$C_{12}$ paraffin, cyclohexane, methylcyclohexane, benzene, toluene, xylenes, and the like.

In the fixed bed operation, the hydrocarbon feed and solvent are fed together to the reactor with hydrogen. Optionally the hydrogen is fed to the reactor at one or two or more positions along the catalyst reaction zone.

In the selective hydrogenation in the catalytic distillation mode, solvent may be introduced at the top of the reactor. The hydrocarbon feed is fed to the catalytic distillation column as vapor at a position below the catalyst bed with hydrogen.

For the purposes of the present invention, the term "catalytic distillation" includes reactive distillation and any other process of concurrent reaction and fractional distillation in a column, i.e., a distillation column reactor, regardless of the designation applied thereto and a "fixed bed" reactor also known as single pass down flow reactor is one in which the reactants and products pass through the reactor in the nature of a plug flow without distillation.

BRIEF DESCRIPTION OF THE DRAWING

The FIGURE is a schematic representation of one embodiment of the present invention.

DETAILED DESCRIPTION

In the present invention, by combining a sequenced fixed bed selective hydrogenation and a catalytic distillation selective hydrogenation the best characteristics of both fixed bed and catalytic distillation operations are adopted for selective hydrogenation of $C_4$ acetylenes in a crude butadiene stream. Since the overall conversion of the acetylenic compounds in the fixed bed is rather high (normally higher than about 80%), the catalyst is most effectively utilized. The desirable composition of the product stream for the second step selective hydrogenation is relatively easily obtained with complete or near complete recovery of 1,3-butadiene by independently controlling all the available process variables. Carrying out the second step selective hydrogenation of remaining acetylenic impurities in the catalytic distillation mode requires the least amount of the catalyst and offers cheaper construction cost, operation cost, longer catalyst service time, and complete recovery of 1,3-butadiene. The combined result is the cheapest cost for construction and operation to completely remove all $C_4$ acetylenic impurities with complete or near complete recovery of 1,3-butadiene with the most effective utilization of the catalyst.

An example of the composition of a steam cracked crude butadiene stream comprises 70 wt. % 1,3-butadiene, 10,000 wt. ppm vinyl acetylene, 2000 wt. ppm ethyl acetylene and 2000 wt. ppm methyl acetylene. When vinyl acetylene in this stream is selectively hydrogenated to about 200 wt. ppm vinyl acetylene, the loss of 1,3-butadiene due to undesired hydrogenation is already high enough. Therefore, further hydrogenation of vinyl acetylene toward completion becomes unacceptable due to the unbearable economical penalty caused by the loss of 1,3-butadiene.

Step 1:

In the first step, $C_4$ acetylenic impurities in a crude butadiene stream are partially hydrogenated over the copper catalyst promoted with palladium disclosed in commonly owned U.S. patent application Ser. No. 09/827,411, hereby incorporated by reference or the improved palladium catalyst disclosed in commonly owned U.S. patent application Ser. No. 09/977,666, hereby incorporated by reference or a combination of these two. Two or more differently optimized catalysts may be loaded in a reactor to obtain the most desirable result. The feed hydrocarbon stream is mixed with hydrogen prior to entering the catalytic hydrogenation reaction zone in fixed bed. One or more reactors are employed for the first step hydrogenation with intermittent cooling between reactors to remove heat of reaction. Optionally, the reactor effluent may be recycled to dilute heat and improve the hydrogenation reaction rates. Another option is employing a solvent such as $C_4$–$C_{10}$ paraffins, cyclo-paraffin such as cyclohexane or methyl cyclohexane, benzene, toluene, ether such as tetrahydrofuran, etc. to slow down the build-up of heavy poisonous polymers on the catalyst. The solvent is recovered from the reactor effluent stream to recycle. Optionally the solvent may be built up in the system at the start-up of the unit, by recycling heavy components, which are usually a small part of feed and are produced by oligomerization and polymerization during the selective hydrogenation in the reactors. Since a part of the heavy components are highly unsaturated which could cause undesirable effects on the catalyst performance, it may be hydrogenated prior to entering the reactors. By choosing a proper set of the process variables such as temperature, pressure, hydrogen gas flow rate, and hydrocarbon feed rate for a given amount of catalyst in the reactor, the selective hydrogenation is performed to obtain a product stream, which has a range of the ratio of vinyl acetylene to ethyl acetylene from 0 to about 1:1, preferably from about 0.01 to 0.6:1 which produces the desired distillation profile for these components in step 2.

Typical conditions for the first fixed bed reactor include a reactor inlet temperature of about 70° F. and outlet temperature of about 120° F., a reactor pressure of about 100 psig, a weight hourly space velocity (WHSV) of between 4 and 8, and a hydrogen flow rate of about 0.1 to 0.2 standard cubic feet per pound of hydrocarbon feed.

Step 2:

It is important to obtain the desired distillation profile of vinyl acetylene, ethyl acetylene and butadienes (normally present as the major component of the feed to the second step, i.e., greater than 50 wt. % of the total stream) for the second step selective hydrogenation in a catalytic distillation reactor. The absolute concentration of vinyl acetylene in the product stream from the first step should be sufficiently low compared with ethyl acetylene. The desired concentration of vinyl acetylene in the feed stream to the catalytic distillation is less than about 1000 wt. ppm, preferably less than 600 wt. ppm, most preferably less than 300 ppm. Yet it is highly desirable to meet the condition of the ratio of vinyl acetylene to ethyl acetylene described above to utilize the best characteristics of catalytic distillation profiles of various components in the feed stream to obtain complete recovery of 1,3-butadiene in the second step. Despite the usual 3 to 6 times higher concentration of vinyl acetylene to ethyl acetylene in a normal steam cracked crude butadiene stream, the desired ratio of vinyl acetylene to ethyl acetylene can be obtained with complete or near complete recovery of 1,3-butadiene in fixed bed operation (the first step).

When a mixture of vinyl acetylene, ethyl acetylene, butadiene and other $C_4$ hydrocarbons is introduced into a catalytic distillation column operating under the selective hydrogenation conditions, the concentration of ethyl acetylene is maximized at a position just below the feed point to the column. But the concentration profiles of vinyl acetylene and 1,3-butadiene are maximized above the feed point. The concentration profiles of vinyl acetylene and 1,3-butadiene above the feed point are partially superimposed from the feed point up. The position of the maximum concentration profile of 1,2-butadiene is located below the feed point. The concentration profiles of various components in the mixed butadiene stream from the first step have a significant role for the complete conversion of $C_4$ acetylenes with a complete recovery of 1,3-butadiene.

The catalyst in the catalytic distillation of the type as described in Step 2 above is loaded in two or more sections. The feed stream from the first step selective hydrogenation is introduced at an appropriate position along the catalyst reaction zone, depending on the composition of the stream from the first step. The hydrogen gas feed is introduced at the bottom of the catalytic distillation column.

The advantages of carrying out the selective hydrogenation in the catalytic distillation mode as disclosed in this invention for the second step are as follows:

1. The maximum utilization of a catalytic reaction zone for the hydrogenation of ethyl acetylene.
2. The most effective hydrogenation of vinyl acetylene, because of relatively low concentration, over a fraction of the catalyst loaded resulting in minimum exposure of 1,3-butadiene to the catalyst, which results in complete recovery of 1,3-butadiene.
3. The favorable profile of hydrogen partial pressure for the hydrogenation of ethyl acetylene because of separation of various components in the feed stream along the column.
4. Long catalyst service life because the catalyst surface is continuously washed down to remove precursors of polymers and polymers, resulting in very slow build up of poisonous carbonaceous materials on the catalyst surface.

The performance of the catalyst deteriorates with on-stream time due to various reasons. One of the reasons is the slow build-up of poisonous carbonaceous materials on the catalyst surface. To prolong the catalyst cycle or service time, a solvent may be fed to the reactor with the feed streams. Solvents include $C_4$–$C_{10}$ paraffinic hydrocarbons, cyclohexane, methyl cyclohexane, benzene, toluene, and ethers such as tetrahydrofuran. The solvent is recovered from the reactor effluent streams to recycle. Optionally the solvent may be built up in the system, at the start-up of the unit, by recycling heavy components which are usually a small part of feed and are produced by oligomerization and polymerization during the selective hydrogenation in the reactors.

It is well known that the palladium-containing catalysts lose palladium because of the formation of soluble palladium-vinyl acetylene complex which results in the loss of the catalyst activity while in service. To compensate for the lost activity of the catalyst, an organometallic palladium compound solution in organic solvent may be added in the front of the catalytic reaction zone.

Referring to the FIGURE, the first step of the present process is carried out in fixed bed reactor 10 containing a bed of the supported Pd modified Cu 12. $H_2$ is fed to the reactor via line 2 and mixed with a typical crude butadiene stream in line 4. The conditions maximize the selective hydrogenation of the vinyl acetylene ink liquid phase up through the catalyst bed 12 and exiting via line 14 and a portion of the cooled liquid effluent returned to feed 4 via line 8 and a portion fed via line 22 to one or more of entry points 22a, 22b and/or 22c along the catalytic distillation reactor 20. The uncondensed material from condenser 6 includes unreacted $H_2$ which is fed via line 16 to a point below the catalytic distillation structures in beds 24, 26, 28 and 30. The heavies distill down and exit via line 32 while the $H_2$ and $C_4$'s including 1,3-butadienes and acetylenes pass up through the column via distillation where substantially all of the acetylenes are converted to olefins and alkanes with very slight loss of the 1,3-butadiene. The $C_4$'s and $H_2$ exit via line 34 and reflux drum 38 where the $C_4$'s are collected as liquid and recovered via line 44 and sent to the separation unit. Conventional coolers 14a and 34a are located along lines 14 and 34 respectively. $H_2$ is vented or recycled to $H_2$ make-up line 18 via line 42. A line 46 is provided to add Pd to the catalyst in reactor 10 to replace that leached out by acetylene.

EXAMPLE 1

This example demonstrates the partial selective hydrogenation of a steam cracked crude butadiene stream in a fixed bed as the first step.

A palladium-promoted copper catalyst is prepared as disclosed in U.S. Ser. No. 09/827,411. A spherically shaped alumina (1.68 mm diameter) is prepared by the oil dropping gelation technique and calcined at 1100° C. for 3 hours. The calcined alumina has the following properties: 67.4 $m^2/g$ BET surface area; average pore diameter of 362Å; 0.701 $cm^3/g$ total $N_2$ pore volume; 0.62 $g/cm^3$ apparent bulk density; 1.45 mm diameter; and mostly theta-alumina with a trace of delta.

300 grams of the above calcined alumina is placed in a rotary impregnator and then a solution prepared by dissolving 28.8 grams $Cu(NO_3)_2.5H_2O$, 10 grams $Zn(NO_3)_2.6H_2O$, and 0.5 grams $AgNO_3$ in 275 grams deionzed water is poured on alumina rolling in the rotary impregnator at 60 rpm. After about 5 minutes cold roll, the alumina is dried by blowing in hot air into the rotary impregnator at 200° C. The dried product is calcined at 450° C. for 2 hours in air. The second impregnation is carried out on this calcined product by using an atomizer (Craftsman, Model No 15002). The calcined product is placed in a rotary impregnator and then a mixed solution prepared by dissolving 4.55 grams $Cu(NO_3)_2.5H_2O$, 3.79 grams $Zn(NO_3)_2.6H_2O$, 0.5 grams $AgNO_3$ and 13.9 grams of Aldrich 10 wt. % palladium nitrate solution (10 wt. % nitric acid) in 140 grams deionzed water is sprayed on the rolling calcined product at 60 rpm for a period of about 25 minutes and then dried by blowing in hot air into the rotary impregnator at about 200° C. The dried product is calcined at 350° C. for 2 hours in air.

The catalyst (50 grams) is mixed with 50 ml of 3 mm diameter glass balls and is loaded in a vertically mounted stainless steel reactor (1 inch diameter×20 inches long). The catalyst is activated by the following procedure: (1) heating the reactor to 235° F. in 200 cc/min $N_2$ gas flow, (2) adding 100 cc/min $H_2$ to the $N_2$ gas flow at 235° F. and then holding for 3 hours at 230° F., (3) shut off $N_2$ gas and increasing $H_2$ gas flow to 300 cc/min, (4) heating the reactor temperature to 550° F. and holding for 3 hours at 550° F. The activated catalyst is cooled to a predetermined temperature for the selective partial hydrogenation of $C_4$ acetylenes in 30 cc/min gas flow of 5 volume % $H_2$ in $N_2$.

The catalyst is tested for the selective hydrogenation of the acetylenic compounds with a steam cracked crude mixed $C_4$ feed stream composed of 0.97 wt. % vinyl acetylene (VA), 0.14 wt. % ethyl acetylene(EA), 0.27 wt. % methyl acetylene(MA), 71.63 wt. % 1,3-butadiene, 0.16 wt. % 1,2-butadiene, 7.80 wt. % 1-butene, and others. The result of this first step of selective hydrogenation is listed in Table 1. The weight ratio of vinyl acetylene to ethyl acetylene in the product stream is 0.

EXAMPLE 2

This example demonstrates the partial selective hydrogenation of $C_4$ acetylenic impurities in a steam cracked crude butadiene stream in a fixed bed as the first step.

A palladium-promoted copper catalyst is prepared. The same alumina is calcined at 1100° C. as in the Example 1. The calcined alumina (300 grams) is placed in a rotary impregnator and then a solution prepared by dissolving 28.8 grams $Cu(NO_3)_2.5H_2O$, 10 grams $Zn(NO_3)_2.6H_2O$, and 0.5 grams $AgNO_3$ in 275 grams deionzed water is poured on the alumina rolling in the rotary impregnator. After about 5 minutes cold roll, the alumina is dried by blowing in hot air into the rotary impregnator at about 200° C. The dried product is calcined at 450° C. for 2 hours in air. The second impregnation is carried out on this calcined product by using a liquid sprayer (not atomizer) made in laboratory. The calcined product is placed in a rotary impregnator. A mixed solution is prepared by dissolving 4.55 grams $Cu(NO_3)_2 \cdot 5H_2O$, 3.79 grams $Zn(NO_3)_2 \cdot 6H_2O$; 0.5 grams $AgNO_3$, and 13.9 grams of Aldrich 10 wt. % palladium nitrate solution (10 wt. % nitric acid) in 140 grams deionized water. This mixed solution is placed in a bomb, and then about 100 psig nitrogen gas pressure is applied to the bomb to push the mixed solution through a small hole to spray on the first impregnation product in a rotary impregnator at 60 rpm. It takes about 20 minutes to complete spraying the solution. The content in the rotary impregnator is dried by blowing in hot air at about 200° C. The dried product is calcined at 350° C. for 2 hours.

The catalyst (36 grams) is mixed with 72 ml of 3 mm diameter glass balls and loaded in a vertically mounted stainless reactor (1 inch diameter×20 inches long). The catalyst is activated by the same procedure used in the Example 1.

The catalyst is tested for the selective hydrogenation of the acetylenic compounds with the same feed as in the Example 1. The test result is listed in Table 1. The weight ratio of vinyl acetylene to ethyl acetylene in the product stream is 0.078.

TABLE 1

Selective Hydrogenation Condition

|  | Example 1 | Example 2 |
|---|---|---|
| Inlet temp. (° F.) | 105 | 99 |
| Outlet temp. (0 F.) | 120 | 120 |
| Press. (psig) | 108 | 108 |
| Hydrocarbon feed rate (WHSV) | 4.4 | 6.1 |
| $H_2$ flow rate (scf/lb of HC) | 0.167 | 0.167 |
| Product |  |  |
| V A (ppm) | 0 | 68 |
| EA (ppm) | 168 | 869 |
| MA (ppm) | 75 | 472 |
| Recovery of 1,3-butadiene (wt. %) | 99.5 | 99.4 |

EXAMPLE 3

In this example, a catalytic distillation column is used for the selective hydrogenation of the acetylenic impurities in the effluent from Example 2. The catalyst (99.88 grams) as described in Example 1 is loaded in a catalytic distillation column (1" diameter×25' height). The height of the catalyst bed in the column is 6 feet. 80 inches of top and bottom of the catalyst bed is packed with ¼" saddles. The catalyst is activated in the same manner described in the Example 1 except that the flow rate of gases is increased proportionally based on the catalyst weight.

The hydrocarbon feed rate is 1.2 pounds per hour. The hydrogen rate is 1 scf per hour at the beginning of the run, but during the run it is changed to higher rates. The hydrocarbon and hydrogen feeds are fed at point between the packing and the catalysts beds. At the hydrogen rate of 3 scf per hour or higher, ethyl acetylene and vinyl acetylene in the feed is practically all removed. Near complete recovery of 1,3-butadiene is obtained.

The invention claimed is:

1. A process for the saturation of acetylenes contained in a butadiene rich stream comprising the steps of:
    (a) feeding hydrogen and a stream containing butadienes and acetylenes to a single pass down flow reactor containing a first hydrogenation catalyst comprising a copper catalyst promoted with palladium wherein less than all of the acetylenes are reacted with hydrogen;
    (b) feeding hydrogen and the effluent from the single pass down flow reactor to a distillation column reactor containing a second hydrogenation catalyst; and
    (c) concurrently in the distillation column reactor;
        (i) reacting a portion of the remaining acetylenes contained within the effluent with hydrogen, and
        (ii) distilling the effluent to remove an overhead and bottoms.

2. The process according to claim 1 wherein said acetylenes comprise vinyl acetylene, ethyl acetylene and methyl acetylene.

3. The process according to claim 2 wherein the ratio of vinyl acetylene to ethyl acetylene in the effluent is in the range of 0.0 to 1.0:1.

4. The process according to claim 2 wherein the ratio of vinyl acetylene to ethyl acetylene in the effluent is in the range of 0.01 to 0.6:1.

5. The process according to claim 1 wherein a solvent is fed to the single pass down flow reactor along with the hydrogen and butadiene stream.

6. The process according to claim 5 wherein the solvent is separated from the effluent and recycled to the single pass down flow reactor.

7. The process according to claim 6 wherein the solvent is selected from the group consisting of $C_4$ to $C_{10}$ paraffinic hydrocarbons, benzene, toluene and ethers.

8. The process according to claim 1 wherein the second hydrogenation catalyst comprises an alumina supported palladium promoted copper catalyst.

9. The process according to claim 1 wherein the second hydrogenation comprises a copper catalyst promoted with palladium, an improved palladium catalyst or combinations thereof.

* * * * *